United States Patent
Prasifka

(10) Patent No.: US 9,726,580 B2
(45) Date of Patent: Aug. 8, 2017

(54) CORN ROOTWORM EMERGENCE CAGE FOR TWO PLANT SYSTEM

(71) Applicant: Dow Agrosciences LLC, Indianapolis, IN (US)

(72) Inventor: Patricia L. Prasifka, Champaign, IL (US)

(73) Assignee: Dow AgroSciences LLC, Indianapolis, IN (US)

( * ) Notice: Subject to any disclaimer, the term of this patent is extended or adjusted under 35 U.S.C. 154(b) by 459 days.

(21) Appl. No.: 13/964,356

(22) Filed: Aug. 12, 2013

(65) Prior Publication Data
US 2014/0060217 A1    Mar. 6, 2014

Related U.S. Application Data

(60) Provisional application No. 61/694,822, filed on Aug. 30, 2012.

(51) Int. Cl.
| | |
|---|---|
| *G01N 1/28* | (2006.01) |
| *A01M 99/00* | (2006.01) |
| *A01G 13/10* | (2006.01) |
| *A01M 5/02* | (2006.01) |

(52) U.S. Cl.
CPC .............. *G01N 1/28* (2013.01); *A01G 13/10* (2013.01); *A01M 5/02* (2013.01); *A01M 99/00* (2013.01)

(58) Field of Classification Search
CPC ...... A01G 13/0256; A01M 1/00; A01M 23/02
USPC ...................... 43/107, 124, 132.1
See application file for complete search history.

(56) References Cited

U.S. PATENT DOCUMENTS

| | | |
|---|---|---|
| 53,772 A | 4/1866 | Beach |
| 131,046 A | 9/1872 | Bailey |
| 6,393,760 B1 | 5/2002 | Lingren |
| 6,754,989 B2 * | 6/2004 | Eicher ................ A01G 13/0256 47/21.1 |
| 2009/0223116 A1 * | 9/2009 | Meghji .................. A01M 1/026 43/118 |

OTHER PUBLICATIONS

Steffey et al. "Transgenic Corn Rootworm Hybrid Stumbles in Urbana Experiment; Some Producers Also Report Severe Lodging with YieldGard Rootworm Hybrids in Commercial Fields" bulletin. ipm.illinois.edu. http://bulletin.ipm.illinois.edu/article.php?id=181 (accessed May 2, 2012).

(Continued)

*Primary Examiner* — Daniel S Larkin
*Assistant Examiner* — Anthony W Megna Fuentes
(74) *Attorney, Agent, or Firm* — Eric J. Kraus; Faegre Baker Daniels LLP

(57) ABSTRACT

Apparatus and methods for monitoring the emergence of soil pests in a two plant system are disclosed. In one embodiment, an emergence cage covers at least a portion of the root system of two plants. The emergence cage includes a frame defining a perimeter, a mesh or screen covering attached to the frame, a first plant opening configured to receive the first plant, a second plant opening configured to receive the second plant, and a collection container for collecting the pest of interest. The pests emerging from the ground under the cage are collected in the collection container, and the number collected is periodically determined.

29 Claims, 5 Drawing Sheets

(56) References Cited

OTHER PUBLICATIONS

Nowatzki et al. "In Field Labeling of Western Corn Rootworm Adults (Coleptera: Chrysomelidae) with Rubidium" Entomological Society of America [Online] 2003, 31, pp. 1750-1759.
Chaddha et al. "Design for an Improved Adult Emergence Trap for Corn Rootworm (Coleoptera: Chrysomelidae)" Journal of the Kansas Entomological Society [Online] 1993, 66, pp. 338-344. (Abstract only).
"Habitat Partioning by Therevids at Sand Ridge State Forest" www.inhs.illinois.edu, http://www.inhs.illinois.edu/inhsreports/jan-feb95/page4.html (accessed May 2, 2012).
Sibbett et al. "Shredding "mummy" walnuts is key to destroying navel orangeworm in winter" California Agriculture [Online], 1993, 47(5), pp. 26-28.
"D. virgifea Larval Movement and Survival is Limited," Publicly available at least since Nov. 2010.
U.S. Environmental Protection Agency (EPA) Office of Pesticide Programs Biopesticides and Pollution Prevention Division (BPPD), "Biopesticides Registration Action Document: MON 89034 x TC1507 x MON 88017 x DAS-59122-7 (SmartStax (R)) B.t. Corn Seed Blend," Nov. 29, 2011 Update, 2011.
U.S. Environmental Protection Agency (EPA) Office of Chemical Safety and Pollution Prevention, Memorandum, "EPA Review of Monsanto and Dow response and supplemental modeling (dated Mar. 18, 2011) to address SAP uncertaintis for a 5% SmartStax . . . " Apr. 4, 2011.

* cited by examiner

CORN ROOTWORM EMERGENCE CAGE FOR TWO PLANT SYSTEM

RELATED APPLICATION

This application claims the benefit of U.S. Provisional Application Ser. No. 61/694,822, filed Aug. 30, 2012, titled CORN ROOTWORM EMERGENCE CAGE FOR TWO PLANT SYSTEM, the entire disclosure of which is expressly incorporated by reference herein.

FIELD

The present invention relates to methods and apparatus studying pest management and in particular to methods and apparatus for studying the movement of soil pests between plants.

BACKGROUND AND SUMMARY

Emergence cages are used in the study of soil pests. Exemplary soil pests include corn rootworm larvae, which feed on the roots of corn plants.

Typical emergence cages cover a single plant or a plurality of plants and an adjacent portion of land. The cages include one or more screens located over the portion of land to prevent emerging adult corn rootworm beetles or other pests from escaping. Pest collection jars positioned at the highest point of the cages allow adult beetles or other pests to enter, but prevents their escape. The collection jars are monitored over a period of time to determine when the adult beetles emerge and in what quantities.

A typical test method assumes a solid test population of rootworm larvae present in the soil of the plants being tested. An emergence cage is placed around a single plant of interest, and the number of beetles trapped in the collection jar over time is monitored. A second emergence cage may be placed around a second plant serving as a control. Comparing the number and timing of beetles captured in the collection jars of the emergence cages provides some indication of the resistance of a plant to root damage from soil pests, such as corn rootworm beetles. In addition to the quantity and timing of beetle emergence, root injury may be evaluated on a 0-3 nodal injury scale as described Node-Injury Scale, Oleson, J. D., Y. Park, T. M. Nowatzki, and J. J. Tollefson. 2005. *J. Econ. Entomol.* 98(1): pp. 1-8. However, neither the typical emergence cage nor node-injury scale methods provide any information regarding movement of pest larvae between plants.

In an exemplary embodiment of the present disclosure, an emergence cage for monitoring the emergence of soil pests in a two plant system is provided. In some embodiments, the cage includes a frame defining a perimeter; a mesh material coupled to the frame, the mesh material allowing air and liquid to pass therethrough but providing a barrier to prevent emerged soil pests from exiting the emergence cage; a base portion having a container opening, a first plant opening configured to receive a first plant, and a second plant opening spaced apart from the first plant opening and configured to receive a second plant, the second plant opening having a first dimension taken along a first axis and a second dimension taken along a second axis perpendicular to the first axis, the second dimension being greater than the first dimension; a first plant seal attached to the first plant opening configured to seal the first plant opening around the first plant; a second plant seal attached to the second plant opening configured to seal the second plant opening around the second plant; and a collection container removably coupled to the container opening.

In another exemplary embodiment of the present disclosure, a method for testing the resistance of a plant to soil pests is provided. The method comprises providing a first plant and a second plant adjacent to the first plant in a contiguous sample of soil, the first plant and second plant each having a root system; treating a ground area proximate one of the first plant and the second plant with eggs of the pest of interest; and covering at least a portion of the root system of the first plant and the second plant with an emergence cage, the emergence cage including a frame defining a perimeter, a mesh material coupled to the frame, a first plant opening configured to receive the first plant, a second plant opening configured to receive the second plant, and a collection container for collecting the pests of interest emerging from the covered portion of the root systems of the first and second plants.

In still another exemplary embodiment of the present disclosure, a method for comparing the resistance of plants having a root system to a soil pest is provided. The method comprises providing a first plant and a second plant adjacent to the first plant in a contiguous sample of soil; providing a third plant and fourth plant adjacent to the third plant in a contiguous sample of soil; treating a ground area proximate the first plant and the third plant with eggs of the pest of interest; covering at least a portion of the root systems of the first plant and the second plant with a first emergence cage and covering at least a portion of the root systems of the third plant and the fourth plant with a second emergence cage, wherein the first and second emergence cages each include a frame defining a perimeter, a mesh material coupled to the frame, a first plant opening configured to receive one plant, a second plant opening configured to receive the other plant, and a collection container for collecting the pests of interest, emerging from covered portions of the root systems of the first and second plants; determining the number of pests collected in the collection containers of the first and second emergence cages; and comparing the number of pests collected in the collection container of the first emergence cage with the number of pests collected in the collection container of the second emergence cage.

The above mentioned and other features of the invention, and the manner of attaining them, will become more apparent and the invention itself will be better understood by reference to the following description of embodiments of the invention taken in conjunction with the accompanying drawings.

DETAILED DESCRIPTION OF THE DRAWINGS

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to studying corn rootworm beetles, it should be understood that the features disclosed herein may have application to the study of other soil pests.

Figure 1:
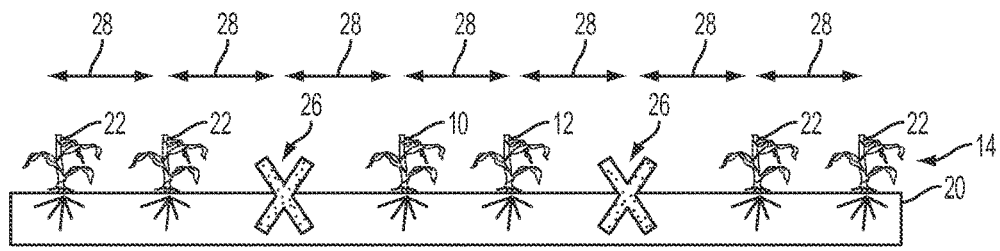
FIG. 1 illustrates a row of plants.

Referring first to FIG. 1, a first plant 10 and a second plant 12 are shown in a row 14 of plants. First plant 10 and second plant 12 include root systems 16 and 18, respectively, in soil 20. Additional plants 22 having root systems 24 are also illustrated in row 14. As illustrated in FIG. 1, the plants immediately adjacent to plants 10, 12, have been removed, leaving spaces 26 between plants 10, 12 and additional plants 22 in row 14. In the illustrated embodiment, the spacing 28 between each plant is substantially the same.

Figure 2:
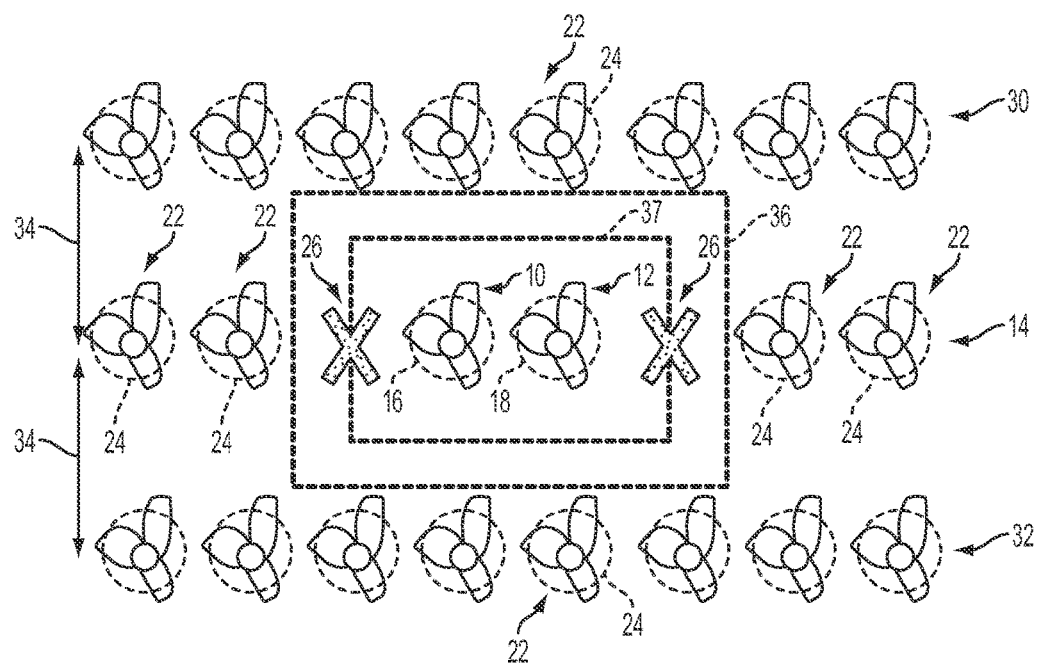
FIG. 2 is a top view illustrating the row of plants of FIG. 1 and adjacent rows.

Referring next to FIG. 2, an overhead view of row 14 of FIG. 1, along with adjacent rows 30, 32 containing additional plants 22 is illustrated. In the illustrated embodiment, the row spacing 34 between row 14 and rows 30, 32 is substantially the same. The root systems 16, 18 of first and second plants 10, 12, and the root systems 24 of additional plants 22 are illustrated as being contained in dashed lines in FIG. 2. An area 36 containing only the root systems 16, 18 of plants 10, 12 is illustrated in FIG. 2. As illustrated, area 36 may include at least some of the spaces 26 formed by removing plants immediately adjacent to plants 10, 12.

Figure 3:
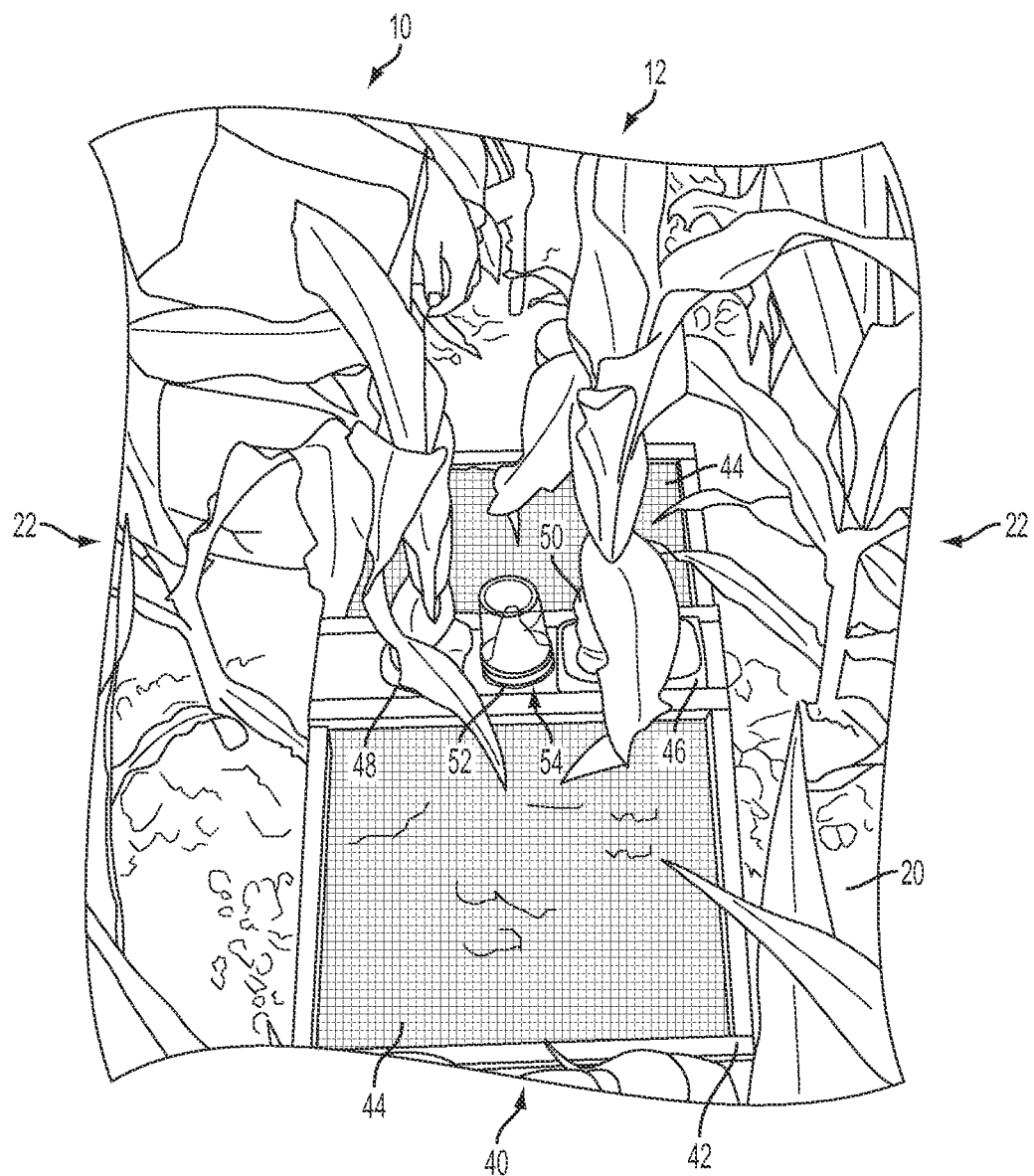
FIG. 3 illustrates an exemplary emergence cage.

Referring next to FIG. 3, an exemplary emergence cage 40 is illustrated surrounding a first plant 10 and a second plant 12. Emergence cage 40 includes a frame 42 defining side walls of emergence cage 40. Frame 42 contacts the soil 20 surrounding the first and second plants 10, 12. In one exemplary embodiment, frame 42 is formed from pieces of wood, but other suitable materials may also be used. In another embodiment, frame 42 includes sheet metal wrapped around a wooden frame.

In one embodiment, frame 42 prevents emerged soil pests from escaping. In the illustrated embodiment, frame 42 defines a perimeter of emergence cage 40, and is placed in an area 36 containing the root systems only of first plant 10 and second plant 12 (see FIG. 2). In one embodiment, frame 42 is positioned in cage area 37 as illustrated in FIG. 2, such that the cage extends about half the distance between plants 10, 12 and additional plants 22 in row 14 and about half the distance between row 14 and adjacent rows 30, 32. In another embodiment, frame 42 covers soil 20 containing at least a portion of the root systems 16, 18 of first plant 10 and second plant 12. In still another embodiment, frame 42 covers soil 20 containing at least a portion of the root systems 16, 18 of first plant 10 and second plant 12 and a portion of a root system 24 of an additional plant 22. In an exemplary embodiment, soil 20 in cage area 37 is loosened with a shovel and emergence cage 40 is placed on the loosened soil 20. Frame 42 is then pushed at least partially into the soil 20, and additional soil 20 is mounded around the edges of frame 42 to provide a seal to prevent emerged soil pests from escaping.

Referring again to FIG. 3, emergence cage 40 also includes a screen or other suitable mesh material 44 coupled to frame 42 and positioned above soil 20. In the illustrated embodiment, mesh material 44 is a metal screen. Other suitable mesh material, including screens or meshes made from cloth, plastic, or other suitable materials, may also be used. Air and water can pass through mesh material 44 to reach the soil 20. Pests emerging from soil 20, such as beetles, are prevented from passing through screen 44. In the illustrated embodiment, mesh material 44 is includes two parts separated by a center section 46 of emergence cage 40. In another embodiment, mesh material 44 is a single piece of material or screen.

Figure 4:
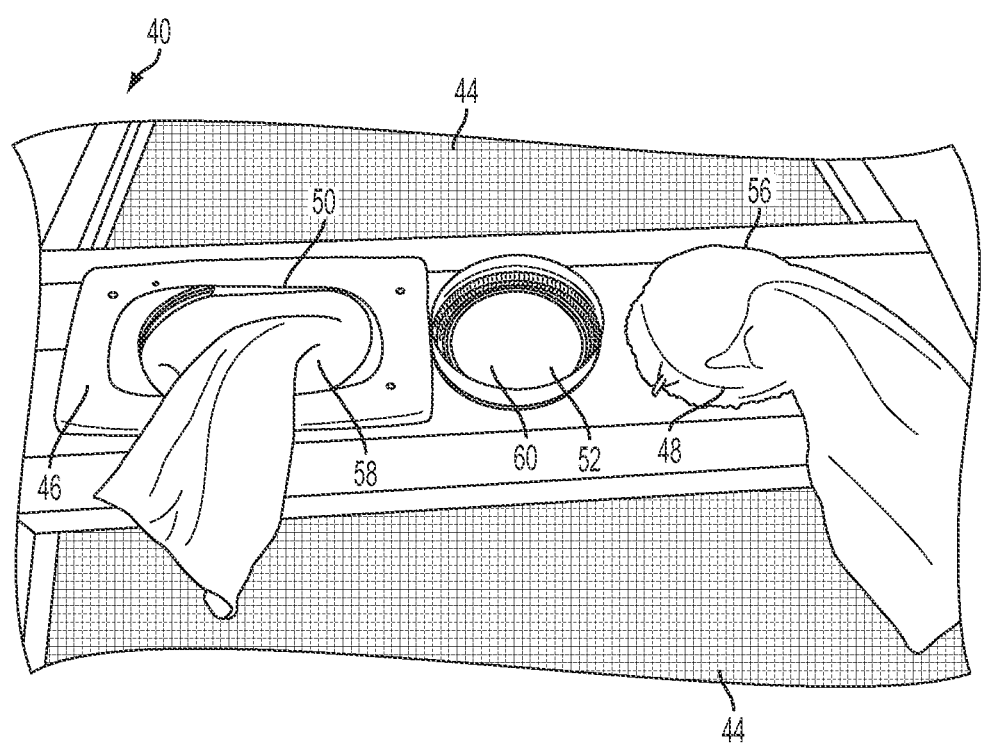
FIG. 4 illustrates a portion of the emergence cage of FIG. 3 illustrating spaced apart openings covered by seals.
Figure 5:
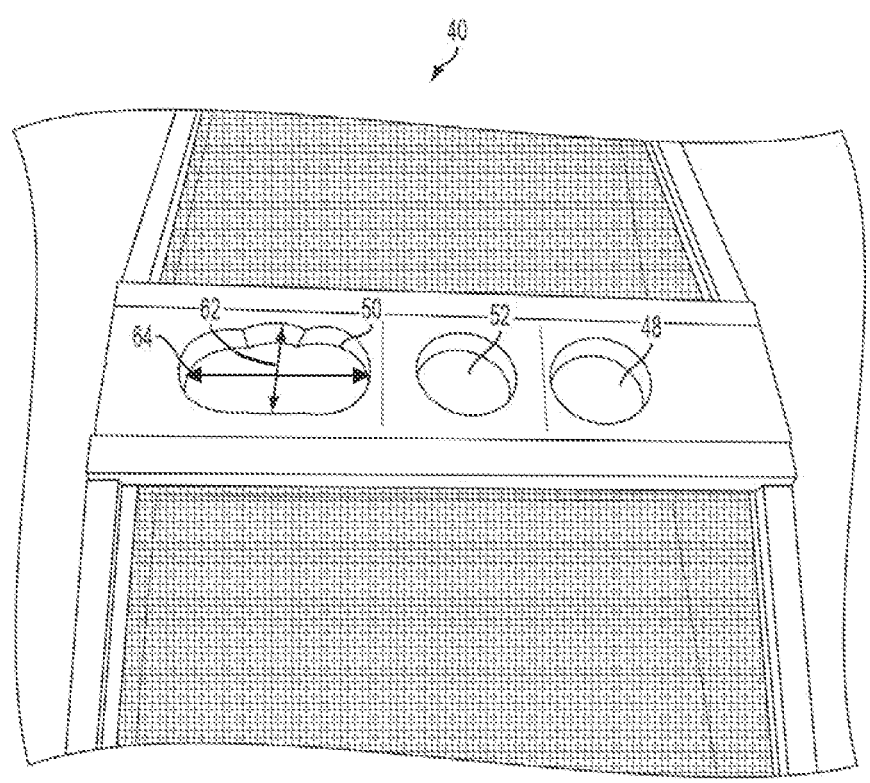
FIG. 5 illustrates the portion of the emergence cage of FIG. 4 with the seals and jar connection removed.

As illustrated in FIG. 3, center section 46 of emergence cage 40 connects opposite sides of frame 42. In the illustrated embodiment, center section 46 is a single piece of wood or other suitable material having three holes formed therein, as best illustrated in FIGS. 4 and 5. A first hole 48 is configured to receive first plant 10. A second hole 50 is configured to receive second plant 12. A collection hole 52 is configured to receive a collection jar 54 for collecting emerging pests, such as corn rootworm beetles.

FIG. 4 illustrates a portion of the emergence cage 40 of FIG. 3. A first seal 56 is attached to first hole 48. In the illustrated embodiment, first seal 56 includes a fabric sleeve. In one embodiment, first seal 56 is placed around first plant 10 when first plant 10 is received in first hole 48. First seal 56 is then tightly secured around a stalk or other portion of first plant 10 positioned in first hole 48 to prevent pests, such as beetles, from exiting emergence cage 40 through first hole 48. In one embodiment, first seal 56 is secured by tightening an elastic band, zip-tie, metal twist-tie, or other suitable tightening means around a fabric sleeve containing first plant 10. The fabric sleeve is then pushed or positioned through first hole 48 so that the tightening means is located below the level of center section 46 of cage 40.

FIG. 4 also illustrates a second seal 58 attached to second hole 50. In the illustrated embodiment, second seal 58 is similar to first seal 56, except that it is larger than first seal 56 to cover the larger second hole 50.

In the embodiment illustrated in FIG. 4, a jar connection 60 is attached to a collection hole 52. A collection jar 54 (see FIGS. 3 and 6) is removably attached to the jar connection 60. In the illustrated embodiment, collection hole 52 is aligned with first hole 48 and second hole 50, which positions the collection jar 54 in the closest position to both first plant 10 and second plant 12 when the plants 10, 12 are received in first and second holes 48, 50, respectively. In another embodiment, collection hole 52 is positioned between, but not aligned with, first hole 48 and second hole 50. In still another embodiment, collection hole 52 is not positioned between the first hole 48 and the second hole 50.

In one embodiment, in which only a single plant system is to be observed, a user can tie off second seal 58 or otherwise close second hole 50 to prevent emerged pests from exiting emergence cage 40 through second hole 50. In this embodiment, first seal 56 is moved from the first hole 48 to the collection hole 52 and secured to the jar connection 60. Collection jar 54 is moved from the collection hole 52 to the first hole 48 and attached to a second jar connection (not shown) similar to jar connection 60 attached to first hole 48. In this embodiment, the first hole 48 and the collection hole 52 are substantially the same size, allowing first plant 10 to be received in the collection hole 52 rather than the first hole 48.

Referring next to FIG. 5, the portion of emergence cage 40 shown in FIG. 4 is shown with the seals 56, 58 and jar connection 60 removed. In the illustrated embodiment, first hole 48 and collection hole 52 are both substantially circular in shape. Other suitable shapes may also be used, and in another embodiment, first hole 48 is a different shape than collection hole 52.

In the illustrated embodiment, second hole 50 is not circular in shape. Second hole 50 has a width dimension 62 and a length dimension 64. As illustrated, the width dimension 62 is perpendicular to a longitudinal axis of center section 46, and the length dimension 64 is aligned with a longitudinal axis of center section 46. In the illustrated embodiment, the length dimension 64 is longer than the width dimension 62. In one embodiment, the width dimension 62 is substantially the same as the diameter of circular first hole 48, and the length dimension 64 is more than twice the length of width dimension 62. In one embodiment, the length dimension is along an axis including first hole 48.

In another embodiment (not illustrated), first hole 48 is not circular in shape. In this embodiment, first hole 48 has a width dimension and a length dimension, the length dimension being greater than the width dimension. In one embodiment, the length dimension of first hole 48 is parallel to the length dimension 64 of second hole 50.

As illustrated in FIG. 5, the second hole 50 is spaced apart from the first hole 48. In one embodiment, the oblong or elongated shape of the second hole 50 allows for different spacing 28 (see FIG. 1) between adjacent plants. In another embodiment (not shown), the oblong or elongated shape of both the first hole 48 and the second hole 50 allows for different spacing 28 (see FIG. 1). In one embodiment, the first hole 48 and second hole 50 are spaced apart such that a first plant 10 and a second plant 12 can be received in first hole 48 and second hole 50 when the spacing 28 between first plant 10 and second plant 12 is as little as 5.0 inches, 5.5 inches, 6 inches, 6.5 inches or as great as 7.0 inches, 7.5 inches, 8.0 inches, 8.5 inches, 9.0 inches, 9.5 inches, 10.0 inches, 10.5 inches, or 11.0 inches, or within a range defined between any pair of the foregoing values. In another embodiment, a maximum value for spacing 28 is greater than 11.0 inches.

Figure 6:
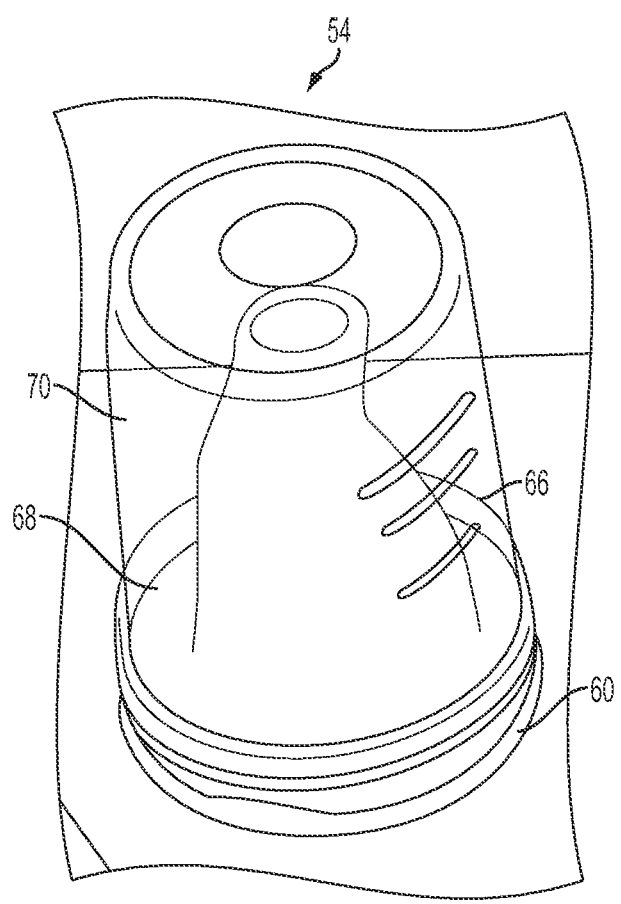
FIG. 6 illustrates an exemplary collection jar.

Referring next to FIG. 6, an exemplary collection jar 54 is shown. Collection jar 54 is removably attached to center section 46 of emergence cage 40 through jar connection 60. In one embodiment, the collection jar 54 includes an outer surface 66 and an inner trap 68. In one embodiment, the outer surface 66 is transparent to allow a user to observe whether pests are currently in the collection jar 54. Exemplary outer surface 66 materials include glass and plastic, although other suitable materials may also be used. In one embodiment, inner trap 68 is conically shaped with a hole at the top to allow pests to enter collection jar 54 but not exit. The illustrated collection jar 54 and jar connection 60 are formed from a Mason jar and ring, respectively. The illustrated inner trap 68 is a conical paper drinking cup with the tip cut off with a pair of scissors. Other suitable collection jars may also be used.

A method of using the emergence cage 40 is provided in an illustrated embodiment of the present disclosure. Referring first to FIGS. 1 and 2, two adjacent plants 10, 12 are selected growing in soil 20 containing no eggs of the pest of interest. Additional plants 22 adjacent to plants 10, 12 are removed, creating an area 36 containing only the roots of plants 10, 12.

For each pair of plants, the first plant 10 and the second plant 12 may be subject to a treatment or not subject to the treatment. In one exemplary embodiment, the treatment may be a pesticide applied to the plant, and neither plant, both plants, or only one of first plant 10 and second plant 12 may be subject to the treatment. In another exemplary embodiment, the treatment may be a gene of interest. Neither plant, both plants, or only one of first plant 10 and second plant 12 may contain the gene of interest. The plant or plants containing the gene of interest may be a transgenic plant.

For each pair of plants selected, the soil 20 containing the roots of one of the plants is infested with eggs of the pest of interest. In one embodiment, this is done by creating one or more shallow holes in the soil 20 containing the roots of the plant and depositing the eggs in the soil. In an exemplary embodiment, several holes, each about 4 inches deep, were created around the plant, and the eggs were divided between the holes. In another exemplary embodiment, a single hole about 4 inches deep was created right next to the plant and all the eggs were placed in the single hole.

An emergence cage 40 is then placed around the two plants 10, 12. The emergence cage 40 is sealed by first seal 56 around first plant 10 and second seal 58 around second plant 12. Collection jar 54 is attached to jar connection 60.

The eggs infested on the infested plant hatch into larvae. The larvae feed on either the roots of the infested plant or travel through the soil 20 to feed on the roots of the non-infested plant. The larvae pupate, and a mature adult beetle emerges and burrows to the surface of soil 20.

The frame 42 and screen 44 of emergence cage 40 cover the root systems 16, 18 of first and second plants 10, 12. At the surface, the adult beetle is trapped in emergence cage 40. The adult beetle will continue moving to the highest point in emergence cage 40 until entering the collection jar 54, where the beetle is trapped.

The collection jar 54 is then removed and the number of beetles trapped in collection jar 54 are counted and recorded. The sex of the beetles may also be determined. The date or number of days since the plant was infested with eggs is also recorded. The collection jar 54 is then emptied of beetles and re-attached to emergence cage 40. In one embodiment, the number of beetles in collection jar 54 is determined weekly until no beetles have been observed for two consecutive weeks. In another embodiment, the number of beetles in collection jar 54 is determined twice a week until no beetles have been observed for two consecutive weeks. Other reading frequencies may also be used, including non-periodic frequencies.

In one embodiment, multiple pairs of plants are selected. In one embodiment, the pairs of plants are selected at random. In one embodiment, pairs of plants are divided into between two and four or more groups for studying the movement of soil pests between plants. The quantity and timing of beetles collected in collection jars 54 between the pairs of plants are compared.

In an exemplary embodiment, the number or timing of beetles collected is compared between one or more of the following first plant 10 and second plant 12 pairs: 1) a pair of untreated plants where one of the untreated plants is infested, 2) a pair of treated plants where one of the treated plants is infested, 3) a treated and an untreated plant where the treated plant is infested, and 4) a treated and an untreated plant where the untreated plant is infested. In these embodiments, the lower the number of beetles collected, the higher the resistance imparted to the treated plant.

EXAMPLE—INVESTIGATING THE MOVEMENT OF *D. VIRGIFERA* LARVAE BETWEEN PLANTS

In this trial, small cages were used to measure *D. virgifera*, western corn rootworm (WCR) adult emergence from pairs of corn plants, one of which was infested with WCR eggs and the other of which was not. This study therefore enables an estimate of the extent and consequences of WCR larval movement between plants in pure stands or in seed mixes. The transgenic plants contained a gene for producing the *Bacillus thuringiensis* toxin (Bt-modified corn plants), while the non-transgenic plants were non-Bt corn plants. All treatments were replicated four times using a randomized complete block design. Plots were four rows wide (30 inch row-spacing) by 20 ft long.

Treatments were as given in Table 1:

TABLE 1

Results of Treating One Plant in a Two-Plant System

| | Infested plant | Uninfested plant | D. virgifera Adult Count |
|---|---|---|---|
| A | non-transgenic | non-transgenic | 46 |
| B | non-transgenic | transgenic | 32 |
| C | transgenic | non-transgenic | 4 |
| D | transgenic | transgenic | 0 |

The trial was conducted on ground that was previously planted to soybeans and had no history of rotation-resistant corn rootworms to ensure the only beetles present were those that were artificially infested. Three pairs of plants (V3 growth stage) in the center two rows of each four row plot were randomly selected. Prior to infestation and cage placement, the corn plants on either side of the selected pairs were removed to ensure larval movement (if any) would only be between the caged plants.

The appropriate plant of the pair as described in the treatment list above was infested with approximately 500 WCR eggs. Eggs were infested by creating two 8 cm deep holes, one on each side of the plant. In each hole, 5 ml of the egg-agar solution (approximately 250 eggs) was placed on each side of the plant using a 10 ml pipette.

Live-plant emergence cages 40 were positioned to accommodate two plants and root systems were contained under each cage 40. The day after eggs were infested, cages 40 were placed over the plant pairs but not sealed so the corn plants could continue to grow normally as the CRW larvae developed. Twenty days later, when larvae had reached the third instar, the cages were sealed and checked every 3-7 days for corn rootworm beetles until no WCR had emerged for two weeks. All beetles obtained from plots were counted.

As shown in the results in Table 1, most larvae infested on a non-transgenic plant remained on the non-transgenic plant. As indicated by the difference between group A and B, a small number of larvae left the non-transgenic plant and died on the transgenic plant. As indicated by group C, a small number of larvae left the transgenic plant and developed on the non-transgenic plant.

While this invention has been described as relative to exemplary designs, the present invention may be further modified within the spirit and scope of this disclosure. Further, this application is intended to cover such departures from the present disclosure as come within known or customary practice in the art to which this invention pertains.

The invention claimed is:

1. A method for testing a plant, the method comprising:
   providing a first plant and a second plant adjacent to the first plant in a contiguous sample of soil, the first plant and second plant each having a root system;
   treating a ground area proximate only one of the first plant and the second plant with eggs of the pest of interest; and
   covering at least a portion of the root system of the first plant and the second plant with an emergence cage, the emergence cage including a frame defining a perimeter, a mesh material coupled to the frame, a center section supported by the frame, a first plant opening in the center section, the first plant opening configured to receive the first plant, a second plant opening in the center section, the second plant opening configured to receive the second plant, the first plant opening and the second plant opening both being laterally centered along a longitudinal direction of the center section of the emergence cage and the second plant opening being spaced apart from the first plant opening along the longitudinal direction, and a collection container for collecting the pests of interest emerging from the covered portion of the root systems of the first and second plants, the collection container being positioned longitudinally between the first plant opening and the second plant opening and being laterally centered along the longitudinal direction of the center section of the emergence cage, wherein the second plant opening has a first dimension taken along a lateral direction and a second dimension taken along the longitudinal direction perpendicular to the lateral direction, the second dimension being greater than the first dimension.

2. The method of claim 1, further comprising determining the number of pests collected in the collection container.

3. The method of claim 1, wherein the first plant is a transgenic plant.

4. The method of claim 3, wherein the ground area treated with eggs of the pest of interest is proximate the first plant.

5. The method of claim 3, wherein the ground area treated with eggs of the pest of interest is proximate the second plant.

6. The method of claim 3, wherein the second plant is a transgenic plant.

7. The method of claim 1, wherein the contiguous sample of soil does not contain the pest of interest prior to the treating step.

8. The method of claim 1, wherein the second axis is aligned with a longitudinal axis of a center section of the frame.

9. The method of claim 1, wherein the first plant opening defines a first continuous perimeter in the center section and the second plant opening defines a second continuous perimeter in the center section.

10. A method for comparing plants having a root system, the method comprising:
    providing a first plant and a second plant adjacent to the first plant in a contiguous sample of soil;
    providing a third plant and a fourth plant adjacent to the third plant in a contiguous sample of soil;
    treating a ground area proximate only the first plant and the third plant with eggs of the pest of interest;
    covering at least a portion of the root systems of the first plant and the second plant with a first emergence cage and covering at least a portion of the root systems of the third plant and the fourth plant with a second emergence case, wherein the first and second emergence cages each include a frame defining a perimeter, a mesh material coupled to the frame, a center section supported by the frame, a first plant opening in the center section, the first plant opening configured to receive one plant, a second plant opening in the center section, the second plant opening configured to receive the other plant, the first plant opening and the second plant opening both being laterally centered along a longitudinal direction of the center section of the emergence cage and the second plant opening being spaced apart from the first plant opening along the longitudinal direction, and a collection container for collecting the pests of interest emerging from covered portions of the root systems of the plants, wherein the collection container is positioned longitudinally between the first plant opening and the second plant opening and is laterally centered along the longitudinal direction of the center section of the emergence cage;

determining the number of pests collected in the collection containers of the first and second emergence cages; and comparing the number of pests collected in the collection container of the first emergence cage with the number of pests collected in the collection container of the second emergence cage.

11. The method of claim 10, wherein the first and second plants are not transgenic hybrids.

12. The method of claim 11, wherein the third and fourth plants are transgenic hybrids.

13. The method of claim 11, wherein the third plant is a transgenic hybrid, and the fourth plant is not a transgenic hybrid.

14. The method of claim 11, wherein the third plant is not a transgenic hybrid, and the fourth plant is a transgenic hybrid.

15. The method of claim 10, wherein the first plant is not a transgenic hybrid, and the second plant is a transgenic hybrid.

16. The method of claim 15, wherein the third and fourth plants are transgenic hybrids.

17. The method of claim 15, wherein the third plant is a transgenic hybrid, and the fourth plant is not a transgenic hybrid.

18. The method of claim 15, wherein the third plant is not a transgenic hybrid, and the fourth plant is a transgenic hybrid.

19. The method of claim 10, wherein the first plant is a transgenic hybrid, and the second plant is not a transgenic hybrid.

20. The method of claim 19, wherein the third and fourth plants are transgenic hybrids.

21. The method of claim 19, wherein the third plant is a transgenic hybrid, and the fourth plant is not transgenic hybrid.

22. The method of claim 19, wherein the third plant is not a transgenic hybrid, and the fourth plant is a transgenic hybrid.

23. An emergence cage for monitoring the emergence of soil pests comprising: a frame defining a perimeter;

a mesh material coupled to the frame, the mesh material allowing air and liquid to pass therethrough but providing a barrier to prevent emerged soil pests from exiting the emergence cage;

a center section having a container opening, a first plant opening configured to receive a first plant, and a second plant opening spaced apart from the first plant opening and configured to receive a second plant, the second plant opening being spaced apart from the first plant opening in a longitudinal direction and having a first dimension taken along a first axis and a second dimension taken along the longitudinal direction a second axis perpendicular to the first axis, the second dimension being greater than the first dimension;

a first plant seal attached to the first plant opening configured to seal the first plant opening around the first plant;

a second plant seal attached to the second plant opening configured to seal the second plant opening around the second plant; and a collection container removably coupled to the container opening, the container opening being positioned longitudinally between the first plant opening and the second plant opening and being laterally centered along the longitudinal direction of the center section.

24. The emergence cage of claim 23, wherein the container opening is positioned between the first plant opening and the second plant opening.

25. The emergence cage of claim 23, wherein the perimeter of the frame is configured to cover root systems of the first and second plants.

26. The emergence cage of claim 23, wherein the second plant opening is configured to receive a second plant that is spaced at any intermediate position from about 5.0 inches to about 11.0 inches from a first plant.

27. The emergence cage of claim 23, wherein the second plant seal is further configured to seal the second plant opening in the absence of a second plant.

28. The emergence cage of claim 23, wherein the second axis of the second opening extends through the first plant opening.

29. The emergence cage of claim 28, wherein the first plant opening has a first dimension taken along an axis parallel to the first axis and a second dimension taken along the second axis, the second dimension of the first opening being greater than the first dimension of the first opening.

* * * * *